US010624856B2

United States Patent
Dharmarajan (10) Patent No.: US 10,624,856 B2
(45) Date of Patent: Apr. 21, 2020

(54) NON-EXTRACTABLE ORAL SOLID DOSAGE FORMS

(71) Applicant: Dharma Laboratories LLC, Morrisville, NC (US)

(72) Inventor: Annadurai Dharmarajan, Morrisville, NC (US)

(73) Assignee: Dharma Laboratories LLC, Morrisville, NC (US)

( * ) Notice: Subject to any disclaimer, the term of this patent is extended or adjusted under 35 U.S.C. 154(b) by 0 days.

(21) Appl. No.: 15/884,745

(22) Filed: Jan. 31, 2018

(65) Prior Publication Data

US 2019/0231698 A1 Aug. 1, 2019

(51) Int. Cl.
| | | |
|---|---|---|
| *A61K 9/20* | (2006.01) | |
| *A61K 9/00* | (2006.01) | |
| *A61K 31/485* | (2006.01) | |
| *A61K 31/551* | (2006.01) | |
| *A61K 31/515* | (2006.01) | |

(52) U.S. Cl.
CPC .......... *A61K 9/2077* (2013.01); *A61K 9/0053* (2013.01); *A61K 9/2009* (2013.01); *A61K 9/2013* (2013.01); *A61K 9/2027* (2013.01); *A61K 9/2031* (2013.01); *A61K 9/2068* (2013.01); *A61K 31/485* (2013.01); *A61K 31/515* (2013.01); *A61K 31/551* (2013.01)

(58) Field of Classification Search
CPC .. A61K 9/2031; A61K 9/2013; A61K 9/0053; A61K 9/5026; A61K 9/5089; A61K 9/2027; A61K 9/2077; A61K 9/2009; A61K 9/2068; A61K 9/5015; A61K 31/551; A61K 31/485; A61K 31/515
See application file for complete search history.

(56) References Cited

U.S. PATENT DOCUMENTS

| | | |
|---|---|---|
| 7,682,634 B2 | 3/2010 | Matthews et al. |
| 8,182,836 B2 | 5/2012 | Mehta |
| 8,420,056 B2 | 4/2013 | Arkenau-Maric et al. |
| 8,647,669 B2 | 2/2014 | Soscia et al. |
| 8,652,529 B2 | 2/2014 | Guimberteau et al. |

(Continued)

FOREIGN PATENT DOCUMENTS

| | | |
|---|---|---|
| EP | 1492505 | 6/2015 |
| WO | 99/32120 | 7/1999 |
| WO | 2008/086804 | 7/2008 |

OTHER PUBLICATIONS

Notification of Transmittal of the International Search Report and the Written Opinion of the International Searching Authority, or the Declaration corresponding to International Application No. PCT/US2018/016105 dated Oct. 18, 2018.

*Primary Examiner* — Hong Yu
(74) *Attorney, Agent, or Firm* — Myers Bigel, P.A.

(57) ABSTRACT

This invention relates to abuse-deterrent pharmaceutical compositions and dosage forms and manufacturing processes thereof, the compositions comprising an agonist and antagonist that are difficult to separate visually, physically, or chemically. The compositions comprise a tacky amorphous polymer and a crystalline polymer curing agent for the amorphous polymer such that the agonist is releasable and the antagonist is non-releasable unless the dosage forms are tampered with. The non-extractable dosage forms reduce the potential for prescription drug abuse.

26 Claims, 2 Drawing Sheets

(56) References Cited

U.S. PATENT DOCUMENTS

| | | |
|---|---|---|
| 8,901,113 B2 | 12/2014 | Leech et al. |
| 9,044,398 B2 | 6/2015 | Hirsh et al. |
| 9,044,402 B2 | 6/2015 | Tygesen et al. |
| 9,101,661 B2 | 8/2015 | McKenna et al. |
| 9,132,096 B1 | 9/2015 | Rekhi et al. |
| 9,456,989 B2 | 10/2016 | Oshlack et al. |
| 2004/0131552 A1* | 7/2004 | Boehm .............. A61K 9/2077 424/10.1 |
| 2011/0212173 A1* | 9/2011 | Young .............. A61K 9/286 424/468 |
| 2016/0106839 A1 | 4/2016 | Barnscheid |

* cited by examiner

NON-EXTRACTABLE ORAL SOLID DOSAGE FORMS

FIELD OF THE INVENTION

This invention relates to abuse-deterrent pharmaceutical compositions and dosage forms and manufacturing processes thereof, the compositions comprising an agonist and antagonist that are difficult to separate visually, physically, or chemically. The compositions comprise a tacky amorphous polymer and a crystalline polymer curing agent for the amorphous polymer such that the agonist is releasable and the antagonist is non-releasable unless the dosage forms are tampered with. The non-extractable dosage forms reduce the potential for prescription drug abuse.

BACKGROUND OF THE INVENTION

Opioids are powerful pain killers and are highly addictive. Opioid dependence affects nearly 5 million people in the United States and leads to approximately 17,000 deaths annually. According to the CDC, rates of opioid overdose deaths jumped significantly, from 7.9 per 100,000 in 2013 to 9.0 per 100,000 in 2014, a 14% increase. In 2015, opioid-involved drug overdoses accounted for 33,091 deaths, approximately half involving prescription opioids.

The treatment of pain and patients' access to needed opioid analgesics has always been in conflict with preventing the misuse and abuse of these potentially addictive medications. With prescription drug abuse growing to epidemic proportions in the United States, it is now becoming significantly important to find effective solutions that lower abuse.

Opioid abusers typically tamper with opioid products in order to extract the active drug which is then smoked, inhaled, or injected intravenously (Webster, *Pain Med.* 10:S124 (2009)). The opioids most likely to be abused are those with long-acting (LA) or extended-release (ER) formulations because each tablet or capsule contains approximately 4 times more opioid than their short-acting or immediate-release (IR) counterparts (see Table 1). The active agent in the ER product is extracted for inhalation, smoking, or injection (Katz et al, *Am. J. Drug Alcohol Abuse* 37:205 (2011)). This involves manipulating the product (typically crushing it, pulverizing it, or dissolving it in solution for use in a syringe) and may also involve chewing the product in an effort to defeat the ER mechanisms. One mode of abuse involves crushing a dosage form (e.g., using a pill crusher, coffee grinder, or hammer) and inhaling or snorting the resultant powder. Another mode of abuse involves extracting the active ingredient with water, alcohol or another solvent or healing the drug to transform it into a liquid to produce a liquid form for injection.

TABLE 1

Comparison of API quantity present in immediate release and controlled release

| Drug | Maximum Strength (API in the dosage form) | |
| --- | --- | --- |
| | Immediate release | Controlled release |
| Oxycodone Hydrochloride | 30 mg | 80 mg |
| Hydrocodone Bitartrate | 10 mg | 50 mg |
| Morphine Sulfate | Not available | 200 mg |
| Hydromorphone Hydrochloride | 8 mg | 32 mg |
| Oxymorphone Hydrochloride | 10 mg | 40 mg |

Technologies have been developed to produce ER opioid formulations designed to resist or deter abuse by making these products harder to crush or dissolve. These so-called abuse-deterrent formulations (ADFs) are now recognized as important tools for the prevention of opioid misuse and abuse, although they cannot completely prevent all abuse. The following products have been approved by the FDA and are currently in the US market.

TABLE 2

FDA approved ADF products

| Product | Abuse-deterrent property | FDA approval date |
| --- | --- | --- |
| OXYCONTIN ® (oxycodone CR tab)† | Mechanical resistance Gelling in solvents | 2010 (original formulation: December 1995) |
| NUCYNTA ® ER (tapentadol ER tab) | Mechanical resistance | 2011 |
| EXAGLO ® (hydromorphone ER tab) | OROS technology, hard outer shell Gelling in solvents | 2010 |
| OPANA ® ER (oxymorphone ER tab) | Crush resistant "Intac technology" by Grunenthal | 2011 |
| OXECTA ® (oxycodone tab) | Gels in liquid Nasal irritant "Aversion technology" by Acura Pharmaceuticals | 2011 |
| EMBEDA ™ (morphine/naltrexone ER cap) | Mixed agonist/antagonist Sequestered antagonist "Intac technology" by Grunenthal | 2009 (Voluntarily Recalled March 2011 and relaunched in 2014) |
| HYSINGLA ® ER (hydrocodone ER tabs | Mechanical resistance Gelling in solvents "Intac technology" by Grunenthal | 2015 |
| MORPHABOND ® ER (Morphine ER tab) | Mechanical resistance Gelling in solvents SentryBond ™ Technology by Inspiron Delivery Science | 2015 |
| XTAMPZA ® ER (oxycodone ER Caps) | Mechanical resistance due to fatty acids Detrex Technology by Collegium | 2016 |
| TROXYCA ® ER (oxycodone ER/ Naltrexone Caps) | Mixed agonist/antagonist Sequestered antagonist | 2016 |
| ARYMO ® ER (morphine ER tabs) | Mechanical resistance Gelling in solvents | 2017 |
| VENTRELA ® ER (hydrocodone ER tab) | Gelling in solvents | 2017 |
| ROXYBOND ® ER (oxycodone IR tab) | Mechanical resistance Gelling in solvents SentryBond ™ Technology by Inspiron Delivery Science | 2017 |

Various abuse reducing approaches are known in the prior art. Approaches based on physical barriers include the following. U.S. Pat. No. 9,132,096 discloses an abuse deterrent dosage form using beads for active ingredient and another set of beads containing gelling agent. U.S. Pat. No. 8,901,113 discloses an abuse deterrent dosage form wherein an active ingredient is combined with a polymer (gel forming agent) to form a matrix. U.S. Pat. No. 8,647,669 discloses a dosage form comprising a drug loaded in a resin and a trap comprises a gelling agent, the TPTA trap comprising a TPTA trap activator, wherein the dosage form comprises a multiplicity of subunits and/or layers. U.S. Pat. No. 9,044, 398 discloses an abuse deterrent dosage form made by forming micro-particles of a drug modified to increase its lipophilicity. The abuse-deterrent composition retards the release of drug, even if the physical integrity of the formulation is compromised. U.S. Pat. No. 8,420,056 discloses a solid administration form, comprising at least one synthetic or natural polymer having a breaking strength of at least 500 N in addition to one or more active substances. U.S. Pat. No. 9,044,402 discloses a controlled release dosage form using polyethylene oxide (PEO) having an average molecular weight of from about 400,000 daltons to about 600,000 daltons along with opioids such that the tablet composition does not provide immediate release of the opioid even after the abuse-deterrent tablet is subjected to physical tampering selected from crushing, grinding, grating, cutting, or crisping, and wherein the tablet composition exhibits a viscosity of at least 170 mPas. U.S. Pat. No. 8,652,529 discloses solid microparticulate oral pharmaceutical forms having a coating layer which assures modified release of the active principle and simultaneously imparts crushing resistance to the coated particles so as to avoid misuse. U.S. Pat. No. 9,101,661 discloses a controlled release dosage form comprising two different molecular weights of polyethylene oxide and its manufacturing process, by which it is abuse resistant from crushing, alcohol extraction and dose dumping to discourage an abuser from tampering with the dosage form.

Approaches using agonist/antagonist combinations include the following. U.S. Pat. No. 7,682,634 discloses a controlled release dosage form comprising an antagonist, an agonist, a seal coat, and a sequestering polymer, wherein the antagonist, agonist, seal coat and at least one sequestering polymer are all components of a single unit, and wherein the seal coat forms a layer physically separating the antagonist from the agonist. U.S. Pat. No. 9,456,989 discloses a sequestered opioid antagonist along with the releasable opioid agonist using hydrophobic polymers for the sequestered antagonist non releasable naltrexone part as coaled beads and uses pH independent beads for the agonist part of the dosage form. U.S. Pat. No. 8,182,836 discloses an opioid antagonist layer coated on an biologically inert pellet, wherein the opioid antagonist layer comprises a therapeutically effective amount of an opioid antagonist; and a non-releasing membrane coated on the opioid-antagonist layer and other beads that have controlled release agonist.

The above patents describing a physical barrier for an abuse deterrent are prone to chemical extraction of the opioid drug. The above patents with sequestered antagonist were coated with a hydrophobic polymer or a polymer that makes the antagonist or naltrexone non-releasable with a controlled release coating whereas the releasable agonist or opioid drug part is made with another or a different polymer than that used to coat the antagonist. Again, this approach means the opioid drug can be extracted using a solvent that dissolves only the polymer in the opioid releasable part whereas the solvent docs not dissolve the polymer coating the non-releasable or sequestered antagonist part.

The abuse deterrent performance of marketed dosage forms has been disappointing. Post-market testing results for oral drug abuse potential are shown in Table 3. The table indicates the data from the oral abuse potential study of FDA approved abuse deterrent formulations from different opioid products. All the products are prone to abuse by the oral route. EMBEDA™ and TROXYCA® contain agonist along with the antagonist as capsules. The antagonist is coated on sugar beads and seal coated by a non-permeable polymer and agonist is coated on top of the antagonist beads coat with a permeable polymer. FDA review has indicated that a certain solvent can extract only the agonist and the dosage form can be abused. The solvent extraction effect has been shown in FDA approved naltrexone sequestered products. EMBEDA™ contains 0.4 mg of naltrexone/5 mg of morphine and TROXYCA® has 0.6 mg of naltrexone/5 mg of oxycodone. Based on the oral abuse potential study, the naltrexone concentration in both products does not deter the abuse potential by the oral route.

TABLE 3

Post-market studies evaluating the oral abuse potential of ADFs

| | | | VAS score, Emax | | |
|---|---|---|---|---|---|
| ADF (n) | Dose | Intact & crushed ADFs & active | Drug liking | Take drug again | Overall drug liking |
| Extended-release (ER) OXYCONTIN® | | No oral abuse potential study | | | |
| χTAMPZA® ER (n = 38) | 40 mg | Xtampza ER- intact | 68.8 | 70.2 | 69.4 |
| | | Xtampza ER- crushed | 73.4 | 73.7 | 74.2 |
| | | IR oxycodone- crushed | 81.8 | 75.4 | 76.2 |
| TROXYCA® ER (n = 4.1) | 60 mg | Troxyca ER- intact | 59.3 | 48.7 | 53.3 |
| | | Troxyca ER- crushed | 74.5 | 72.5 | 74.3 |
| | | IR oxycodone- crushed | 89.8 | 81.5 | 81.8 |
| TARGINIQ™ ER (n = 29) | — | Targiniq ER-intact | 54.7 | 38.5 | NR |
| | | Targiniq ER-chewed | 54.6 | 32.6 | NR |
| | | Oxycodone IR solution | 77.9 | 61.4 | NR |
| HYSINGLA® ER (n = 35) | 60 mg | Hysingla ER- intact | 63.3 | 32.6 | 54.9 |
| | | Hysingla ER- crushed | 69 | 43 | 56.8 |
| | | Hydrocodone IR solution | 94 | 86.7 | 84.1 |
| VENTRELA® ER (n = 41) | 45 mg | Vantrela ER- intact | 53.9 | 46.4 | 49.2 |
| | | Vantrela ER- crushed | 66.9 | 58.7 | 59 |
| | | Hydrocodone IR | 85.2 | 75.2 | 75 |
| EMBEDA™ (n = 33) | 120 mg | Embeda- crushed | 65.2 | 57.7 | 58.6 |
| | | Morphine sulfate ER- crushed | 80.8 | 70.7 | 69.8 |
| EMBEDA™ (n = 32) | 120 mg | Embeda- intact | 67.6 | NR | NR |
| | | Embeda- crushed | 68.1 | NR | NR |
| | | Morphine solution | 89.5 | NR | NR |

TABLE 3-continued

Post-market studies evaluating the oral abuse potential of ADFs

| | | | VAS score, Emax | | |
|---|---|---|---|---|---|
| ADF (n) | Dose | Intact & crushed ADFs & active | Drug liking | Take drug again | Overall drug liking |
| MORPHABOND ® ER | | No oral abuse potential study | | | |
| ARYMO ® ER (n = 38) | 60 mg | Arymo ER- intact | 62 | 56 | 57 |
| | | Arymo ER- crushed | 67 | 61.5 | 63.5 |
| | | Morphine sulfate ER- crushed | 74 | 68 | 67.5 |

Source: Institute for clinical and economic review 2017

In EMBEDA™, the antagonist naltrexone, which is sequestered in the core of each bead, remains latent if the drug is taken as prescribed. However, if the beads are crushed, the antagonist is released and reduces the effects of the morphine. A Phase III trial demonstrated efficacy in pain relief. Data released in the abstract indicate that the morphine pharmacokinetic profile of EMBEDA™ crushed and swallowed is similar to that of immediate-release morphine, but in liking studies EMBEDA™ crushed is "liked" no more than EMBEDA™ taken whole. Co-ingestion of alcohol may result in an increase in plasma levels and potentially fatal overdose of morphine.

These data clearly indicate that currently FDA approved products do not offer adequate oral abuse deterrent properties. This data also indicate that 0.4 mg or 0.6 mg of naltrexone/5 mg of an opioid is insufficient to act as an abuse deterrent in agonist/antagonist combination products. A higher dose of naltrexone is required to act as an abuse deterrent. The current FDA approved dose of naltrexone for opioid abuse deterred is 25 mg to 150 mg naltrexone tablets. Other products like OXYCONTIN®, MORPHABOND® and ARYMO® extended release tablets using other technologies also do not deter the abuse potential by the oral route.

All of the FDA approved extended release opioid products have a warning on the label indicating that these opioid products should not be taken with alcohol. It is also reported in the clinical data of TROXYCA® ER capsules in 40% alcohol showed a 6.4-fold higher $C_{max}$, OPANA® ER a 2.7-fold higher $C_{max}$, NUCYNTA® ER a 4.38-fold higher $C_{max}$, and EMBEDA™ ER a 5-fold higher $C_{max}$.

The data from the oral abuse potential study and the alcohol dose dumping study on FDA approved abuse deterrent products shows clearly that there is a need for improved abuse deterrent opioid formulations required to prevent opioid abuse deaths. A need still exists for an effective treatment of pain with opioids and other abuse potential drugs which are non-extractable with higher patient compliance and deterrence of the abuse potential.

SUMMARY OF THE INVENTION

Tablets, capsules, and lozenges are products classified as oral solid dosage forms. They require excipients that are free flowing, so that they can be compressed into tablets without any manufacturing issues of sticking, capping, and quality issues of content uniformity. A typical tableting process involves mixing excipients with drug, and making a granulation using a binder in purified water or a solvent, so that drug is locked with the excipients after drying. It is milled to achieve uniform granule size and blended with glidants and lubricants, which will make the granules flow easily from the hopper to the compression chamber or between the upper and lower compression punches. Once the granules are in the compression chamber, they are compressed into tablets. During the compression process, 5 to 10 tons of pressure is exerted on a tablet. If there is a coated bead for compression, due to the high pressure of 5 to 10 tons exerted on the coated beads, the coating gets ruptured and the drug content will get released. In order to prevent the rupture of the coated beads and avoid release of significant amounts of drug, most of the coated bead formulations are filled as capsules. Examples include EMBEDA™ capsules (morphine-releasable/naltrexone-sequestered) and TROXYCA® (oxycodone-releasable/naltrexone-sequestered).

The present invention uses on amorphous polymer, which is highly tacky and does not flow well. As a standalone this polymer cannot be processed into free flowing granules. A crystalline polymer is added to convert the tacky amorphous polymer into u non-tacky polymer complex, which makes readily flowable granules alter milling, which can be compressed into tablets.

Tackifier is added, which re-tackifies the amorphous polymer by heating of the tablets. The tackiness of the amorphous polymer prevents extraction of the drug by solvents and makes the formulation a non-extractable oral solid oral dosage form (NEOSD).

The present invention provides a pharmaceutical composition (e.g., NEOSD) that reduces the potential of abuse or misuse of opioids and other drugs of abuse by extraction using home tools and solvents that are commonly used by recreational drug abusers. Methods to process and manufacture NEOSD formulation arc also provided.

Thus, one aspect of the invention relates to a non-extractable oral solid dosage form comprising two different particles (e.g., granules, spheroids, beads or pellets), the first particle comprising:
   i) a tacky amorphous polymer;
   ii) a crystalline polymer curing agent for the amorphous polymer;
   iii) an agonist active pharmaceutical ingredient:
   iv) a channelizer; and
   v) a tackifying agent;
the second particle comprising:
   i) a tacky amorphous polymer;
   ii) a crystalline polymer curing agent for the amorphous polymer:
   iii) an antagonist to the active pharmaceutical ingredient;
   iv) optionally a channelizer; and
   v) a tackifying agent;
wherein the agonist is releasable and the antagonist is substantially non-releasable upon oral administration of the dosage form.

A further aspect of the invention relates to a method of producing the non-extractable oral solid dosage form of the invention, wherein the process comprises:
a) preparing the first particle by:
   i) heating the tacky amorphous polymer above 80° C.;
   ii) adding the agonist and mixing;
   iii) adding the channelizer, crystalline polymer curing agent, and tackifying agent to produce a non-tacky and free flowing mixture; and
   iv) milling and blending the mixture;
b) preparing the second particle by:
   i) heating the tacky amorphous polymer above 80° C.;
   ii) adding the antagonist and mixing;
   iii) adding the crystalline polymer curing agent and tackifying agent to produce a non-tacky and free flowing mixture; and
   iv) milling and blending the mixture;
c) combining the first and second particle into a mixture;
d) compressing the mixture; and
e) curing the mixture, wherein the amorphous polymer becomes re-tackified.

A further aspect of the invention relates to a method of decreasing the abuse potential of an agonist active pharmaceutical ingredient oral solid dosage form, the method comprising preparing the non-extractable oral solid dosage form of the invention.

An additional aspect of the invention relates to a method of administering an agonist active pharmaceutical ingredient to a subject in need thereof, comprising administering the non-extractable oral solid dosage form of the invention to the subject.

These and other aspects of the invention are set forth in more detail in the description of the invention below.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, nucleotide sequences, amino acid sequences and other references mentioned herein are incorporated by reference in their entirely.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompasses any type of prophylactic treatment that reduces the incidence of the condition or delays the onset and/or progression of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

An "agonist," as used herein, refers to an agent that binds to and activates a receptor to produce a biological effect.

An "antagonist," as used herein, refers to an agent that binds to and inhibits activation of a receptor, e.g., blocks the effect of an agonist on the receptor.

The present invention is based on the development of a non-extractable oral solid dosage (NEOSD) pharmaceutical compositions and an antagonist/agonist, two drug combination which will improve patient compliance by alleviating the potential side effects of the opioid drugs. As used herein, the term "non-extractable" refers to a dosage form in which the agonist cannot be readily removed from the dosage form without also removing the antagonist, i.e., the agonist cannot be readily separated from the antagonist. The NEOSD composition opioid products will reduce the improper tampering, misuse, and abuse of prescription opioid products by recreational abusers. The technology may be useful for other abusable drugs where extended release, controlled release, or immediate release by oral delivery is desired, e.g., for 1 to 4 hour or 12 to 24 hour drug release.

In some embodiments, the solid oral product is formulated into a matrix tablet using a tacky amorphous polymer and an optionally crystalline active pharmaceutical ingredient (API), and further comprising water insoluble, non-swellable, non-film forming, inert materials. In some embodiments, the tacky amorphous polymer is blended with the API and cured with a crystalline polymer curing agent to make it non-tacky and form the dosage form, and then the amorphous polymer is converted back into tacky material, which will hold the API and provide a non extractable oral solid dosage form.

The amorphous polymer is very tacky and is not free flowing so it cannot be made into a tablet. As used herein, the term "tacky" refers to a product that is sufficiently sticky that it is not free flowing and is not suitable for tableting. When it is cured with a crystalline polymer it becomes non-tacky and free flowing, and with the drug added along with the channeling agent, it is formed into a dosage form that will release the agonist drug. A similar process is used for the antagonist drug but without the channeling agent, so that the dosage form does not release any of the antagonist.

By addition of the tackifying agent during granulation and heating of compressed tablets, this process makes the amorphous polymer tacky again. The tackiness of the amorphous polymers causes them to fuse together and cover the exposed part (which happens during the milling of granules) of the antagonist granules with the amorphous polymers, covering the milled edges of the granules and making the antagonist pan non-releasable. Upon healing, the amorphous polymers form a very flexible tacky polymer, which adheres to adjacent amorphous polymers and engulfs the antagonist drug. When the polymer is cooled, it locks the antagonist drug and inhibits its release (see Table 4). When the NEOSD is physically tampered with (e.g., cut into pieces, or milled in a coffee grinder or pulled apart), the amorphous polymer surrounding the antagonist is pulled apart and it exposes the antagonist, making the dosage form abuse deterrent.

TABLE 4

| Description | % of naltrexone release, at 24 hours using paddle @100 rpm in 900 ml purified water |
| --- | --- |
| Non-heated tablets | 23.7% |
| Heated for 4 hours | 15.1% |
| Heated for 28 hours | 5.7% |

The amorphous polymer used in the invention has very low moisture vapor transmission rate and also is insoluble, making it nearly impossible for any solvent or water to penetrate and make the agonist or antagonist drug soluble for dissolution. This low moisture vapor transmission rate in the amorphous polymers covering the agonist also reduces or eliminates the alcohol dose dumping phenomenon.

If a polymer with high moisture vapor transmission rate coated or encased the antagonist it will increase the osmotic pressure inside the sequestered antagonist granules or coated particles and it will release the antagonist, preventing sequestration.

Figure 1:
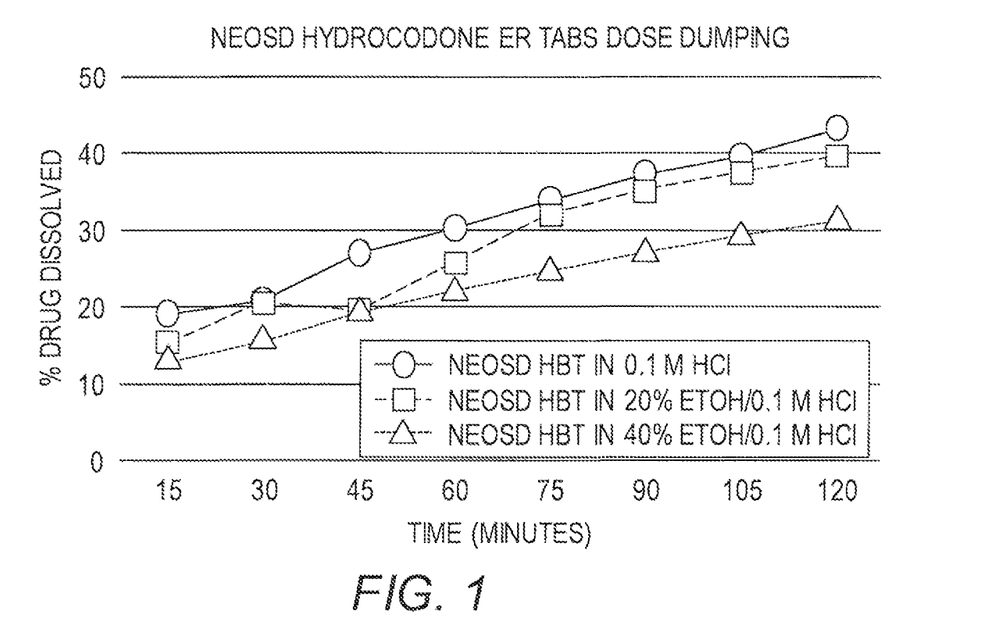
FIG. 1 shows an alcohol dose dumping study with extended release hydrocodone bitartrate tablets.

The prevention of the alcohol dose dumping is shown in the dissolution performance of NEOSD hydrocodone bitartrate extended release tablets in 0.1 N hydrochloric acid, 20% alcohol and 40% alcohol (FIG. 1). The tablet formulation is shown in Table 5. The NEOSD hydrocodone bitartrate extended release tablets showed 43% drug release in 2 hours, compared to 40% release in 20% alcohol, followed by 31.3% release in 40% alcohol. This demonstrates that as the alcohol concentration goes up, the drug release decreases.

TABLE 5

| Ingredient | mg/tablet | grams/batch of 1000 tabs |
| --- | --- | --- |
| Hydrocodone Bitartrate | 10 | 10 |
| Naltrexone Hydrochloride | 4 | 4 |
| Polyisobutylene | 46.8 | 46.8 |
| Polyvinyl Acetate | 106 | 106 |
| Colloidal silicon dioxide | 0.2 | 0.2 |
| Talc | 4 | 4 |
| Mineral oil | 2 | 2 |
| Stearic acid | 7 | 7 |

In some embodiments, the NEOSD is formed by a hot-melting process. In some embodiments the formulation contains sensory agents, which will not release from the tablets over a period of 12 or 24 hours, but will be released when the oral dosage form is physically altered. In some embodiments, the composition contains additional excipients, e.g., softeners, channelizers, and anti-oxidants.

Advantageously, when the physical integrity of the NEOSD dosage form is compromised or altered (e.g., by crushing with a hammer or a pill crusher or grinding with a coffee grinder and the resulting material is placed in water or by heating in a microwave in the presence of water and the resulting material is placed in water or alcohol) the API release is accompanied by release of the antagonist and/or sensory agents, which deters the snorting, chewing, or injecting of the product to get "high." However, if the dosage form is administered intact, the API will release slowly as desired for a period of time, e.g., 1 to 4 hours or 12 to 24 hours.

The NEOSD extended release opioid drug will improve patient compliance by reducing the opioid tolerance due to the very low release of naltrexone. Burns (*Opiate Receptors and Antagonists* pp 247-261 (2009)) indicated ultra-low-dose opioid antagonist co-treatment was first shown paradoxically to enhance opioid analgesia and to reduce analgesic tolerance and physical dependence. Naltrexone is an opiate antagonist, a blocker at the endorphin system. There are two ways that Low Dose Naltrexone (LDN) may be beneficial. It could block the endorphin system for short periods in order to block unwanted effects. Or it could block the endorphin system for a short period of time so that the endorphin system will build itself back up in response and be "supercharged" after the LDN wears off. This could even increase the amount of endorphin in the body. The endorphin system is very intricate and it may be that LDN both blocks some parts of the endorphin system and supercharges other parts. NEOSD technology uses higher amounts of naltrexone as sequestered, but at the same time, it releases low amounts of naltrexone, where it reduces the opioid tolerance (opioid administration over a period of use forms tolerance, and higher doses have to be administered to relieve pain), so NEOSD release of low doses of naltrexone will improve patient compliance against opioid tolerance. The oral solid dosage form disclosed herein may optionally contain an opioid drug which is free from abuse potential.

Thus, one aspect of the invention relates to a non-extractable oral solid dosage form comprising, consisting essentially of, or consisting of two different particles, the first particle comprising, consisting essentially of, or consisting of:
  i) a tacky amorphous polymer;
  ii) a crystalline polymer curing agent for the amorphous polymer;
    iii) an agonist active pharmaceutical ingredient;
    iv) a channelizer; and
    v) a tackifying agent;
the second particle comprising, consisting essentially of, or consisting of:
  i) a tacky amorphous polymer;
  ii) a crystalline polymer curing agent for the amorphous polymer;
    iii) an antagonist to the active pharmaceutical ingredient;
    iv) optionally a channelizer; and
    v) a tackifying agent;
wherein the agonist is releasable and the antagonist is substantially non-releasable (provides no significant release) upon oral administration of the dosage form. In some embodiments, the second particle does not comprise a channelizer.

In some embodiments, the dosage form provides immediate release of the agonist. In some embodiments, the dosage form provides controlled release of the agonist. The dosage form may be adjusted to provide any desirable time frame for release of the agonist, e.g., 1-4 hours, 4-8 hours, 8-12 hours, 12-24 hours, 24-48 hours, 48-72 hours, or any range therein.

The oral solid dosage form may be a unit dosage form, e.g., in any form suitable for oral delivery of a drug, including, without limitation, a tablet, capsule, microcapsule, granule, pellet, lollipop, or lozenge.

In some embodiments, the dosage form is a tablet. The tablet may be in any format that is suitable for oral delivery of a drug. In certain embodiments, the tablet is a matrix tablet, e.g., a tablet having a homogenous core which may be coated or uncoated. In some embodiments, the first and second particles are intermingled uniformly in the matrix. In certain embodiments, the tablet is a multilayer tablet, e.g., a bilayer tablet, in which at least some of the first and second particles are in different layers. In some embodiments, the first particle may be in one layer and the second particle in a different layer. In other embodiments, one layer may contain both the first and second particle while a different layer contains only the first particle or only the second particle. The layers may also differ in terms of the excipients present.

The NEOSD technology of the present invention provides tablets that generally do not break when subjected to typical hardness tests. This may be due to the amorphous polymer forming an integrated tackiness with limited flexibility after curing. When measured for tablet hardness using compression force (e.g., using a texture analyzer such as a Brookfield CT3 Texture Analyzer), the dosage form may exhibit a force of at least 6000 g (e.g., at least 8000, 10000, or 12000 g) when compressed to 30% of its thickness.

In certain embodiments, the first particle and the second particle may contain the same tacky amorphous polymer and/or crystalline polymer curing agent. For example, the particles may contain the same tacky amorphous polymer but different crystalline polymer curing agent, the same crystalline polymer curing agent but different tacky amorphous polymers, or different tacky amorphous polymers and different crystalline polymer curing agents. In some embodiments, the first and/or second particle may contain two or more different tacky amorphous polymers, e.g., 2, 3, 4, 5 or more different tacky amorphous polymers. The tacky amorphous polymers may be different types of polymers or may be the same polymer but having different average molecular weights. In some embodiments, the tacky amorphous polymer in the second particle has a lower molecular weight than the tacky amorphous polymer in the first particle. In certain embodiments, the first particle may have higher molecular weight amorphous polymers on average than the second particle. In some embodiments, the first particle contains a first tacky amorphous polymer having a high molecular weight and a second tacky amorphous polymer having a low molecular weight and/or the second particle contains a first tacky amorphous polymer having a low molecular weight and a second tacky amorphous polymer having a low molecular weight. As used herein, high molecular weight polymer refers to an average molecular weight range of about 500,000 to about 3,000,000 g/mol and low molecular weight polymer refers to a molecular weight range of about 40,000 to about 400,000.

Advantageously, the first and second particles are difficult to separate by any means so that the agonist cannot be separated from the antagonist. In some embodiments, the first particle and the second particle cannot be visually distinguished. In some embodiments, the first particle and the second particle cannot be physically or chemically separated, e.g., using a filter or a solvent. In some embodiments, any solvent that dissolves the tacky amorphous polymer in the first particle to extract the agonist also dissolves the tacky amorphous polymer in the second particle, thereby extracting the agonist and antagonist together.

Advantageously, the NEOSD compositions of the invention are not susceptible to (i.e., eliminate) alcohol-induced dose dumping (ADD) of the agonist. ADD can result in the premature and exaggerated release of a drug. This can greatly increase the concentration of a drug in the body and thereby produce adverse effects or even drug-induced toxicity.

Advantageously, the NEOSD compositions of the invention release the agonist in a pH independent fashion, e.g., independently of the pH of a physiological dissolution medium. This may prevent extraction of the agonist using acids or bases.

The agonist in the first particle may be present in any suitable amount to provide a therapeutic or prophylactic effect. In some embodiments, the amount of agonist in the first particle is about 0.1% to about 30% w/w or more of the total dosage form, e.g., about 0.1%, 0.5%, 1%, 2%, 3%, 4%, 5%, 10%, 15%, 20%, 25%, 30%, or any range therein.

The agonist may be any API that has a therapeutic or prophylactic effect and which has a known antagonist. The agonist may be one that is susceptible to abuse, e.g., one that is a Drug Enforcement Authority controlled substance. In some embodiments, the agonist is a central nervous stimulant, opioid, barbiturate, benzodiazepine, or sedative. In some embodiments, the drug or API is crystalline in form.

The terms "drug" and "active pharmaceutical ingredient" are used interchangeably herein to refer to a chemical compound that induces a desired pharmacological, physiological effect. The terms also encompass pharmaceutically acceptable derivatives of those active agents specifically mentioned herein, including, but not limited to, salts, stereoisomers, solvates, hydrates, complexes with one or more molecules, prodrugs, active metabolites, lipophilic derivatives, analogs, and the like. Suitable drugs include, without limitation, amobarbital, alphacetylmethadol, apomorphine, apocedeine, alfentanil, allylprodine, alphaprodine, anileridine, benzylmorphine, bezitramide, buprenorphine, butorphanol, butabarbital, clonitazene, codeine, clonazepam, cycazocaine, cyclophen, cyprenorphine, desomorphine, dextromoramide, dezocine, diazepam, diampromide, diamorphone, dihydrocodeine, dihydromorphine, dimenoxadol, dimephepianol, dimethylthiambutene, dioxaphetyl butyrate, dipipanone, eplazocine, ethoheptazine, elhylmethylthiambutene, ethylmorphine, etonilazene, etorphine, dihydroelorphine, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, naltrexone, naloxone, nalmefene, methylnaltrexone, naloxone methiodide, nalorphine, naloxonazine, nalide, nalmexone, nalbuphine, nalorphine dinicotinate, opium, oxycodone, oxymorphone, papavetetum, pentazocine, phenadoxone, phenomorphan, phenazocine, phenoperidine, piminodine, piritramide, propheptazine, promedol, properidine, propoxyphene, sufentanil, tilidine pentazocine, dezocine, talbutal, thebaine, thiamylal, thiopental, tramadol, trimeperidine, vinbarbital and Cox2 inhibitor drugs, or their pharmacologically effective esters or salts.

The antagonist may be present in the dosage form in an amount sufficient to at least partially inhibit, but preferably fully inhibit, the activity of the agonist. The amount of antagonist may be sufficient to inhibit at least about 10%, 20%, 30%, 40%, 50%, 60%, 70%, 80%, or 90% or more of the activity of the agonist. In one embodiment, the dosage form may comprise about 0.25 mg to about 5.0 mg of antagonist per 5 mg of agonist, e.g., about 0.25, 0.5, 1.0, 1.5, 2.0, 2.5, 3.0, 3.5, 4.0, 4.5, or 5.0 mg antagonist or any range therein per 5 mg of agonist.

In some embodiments, the agonist is an opioid and the antagonist is an opioid antagonist. An opioid receptor antagonist is a receptor antagonist that acts on one or more of the opioid receptors. Naloxone and naltrexone arc commonly used opioid antagonist drugs which arc competitive antagonists that bind to opioid receptors with higher affinity than agonists hut do not activate the receptors. This effectively blocks the receptor, preventing the body from responding to opioids. The opioid antagonist may be, without limitation, naloxone, nalmefene, naltrexone, or any other known or later developed opioid receptor antagonist.

The opioid receptor antagonists naloxone and naltrexone are competitive antagonists at the mu, kappa, and delta receptors, with a high affinity for the mu receptor but lacking any mu receptor efficacy. Naltrexone hydrochloride is a pure opioid antagonist. It markedly attenuates or completely blocks, reversibly, the subjective effects of all opioids. When co-administered, on a chronic basis, naltrexone hydrochloride blocks the physical dependence to morphine, heroin and other opioids. Naloxone and naltrexone act centrally and peripherally. Naloxone has low oral bioavailability, but a fast onset of action following parenteral administration. Naltrexone is orally effective with a long duration of action making it useful in abuse deterrent. Nalmefene, a mu-opioid receptor antagonist, is a water-soluble naltrexone derivative with a longer duration of action than naloxone.

Naltrexone is an orally available semisynthetic opiate antagonist, a synthetic derivative of oxymorphone, approved by the FDA and marketed as REVIA® with a 50-150 mg daily dose. Naltrexone and its main active metabolite, 6-beta-naltrexol, are competitive antagonists at mu- and ka-opioid receptors and less at delta-opioid receptors. They reversibly block or significantly attenuate the subjective effects of opioids/classic morphine-like opiates and analgesics with agonist and antagonist activity. Its bioavailability is 5 to 40%. It is well absorbed in the gastrointestinal tract and has a first-pass hepatic metabolism. Plasma protein binding is 21%. The half-life of naltrexone is 4 hours and of 6-beta-naltrexol is 16 hours. It is used in the treatment of heroin and alcohol addiction because it counteracts the effects of opioids by blocking opiate receptors. Dosages range from 25 mg to 150 mg. When blockade is adequate this dose blocks 25 mg heroin administered intravenously. When naltrexone is given at a lower dose, equal to or less than 5 mg/day (low-dose naltrexone (LDN)), its opiate antagonist activity turns into an agonist one, so as to trigger a prolonged release of endogenous opioids such as β-endorphins.

Unintended early and severe precipitation of opiate withdrawal may occur when opiates have been taken 7-10 days prior to the beginning of naltrexone application. Precipitated withdrawal occurs when a full agonist, such as heroin, is displaced from opioid receptors by an antagonist, such as naloxone. Precipitated withdrawal is similar to regular withdrawal but is more intense and has a much faster onset.

The order of potency to block analgesia is naltrexone>naloxone>6β-naltrexol. The order of potency to precipitate withdrawal jumping is naltrexone>naloxone>>>6β-naltrexol.

The utility of opioid antagonists to reverse the action of opioid agonists is well established. Opioid antagonists (e.g., naltrexone and naloxone) have a long clinical history in the management of opioid overdose. However, in opioid overdose situations, administration of an opioid antagonist can induce an acute withdrawal syndrome that could be life-threatening.

The present invention involves a sequestered antagonist such as naltrexone. When the dosage form is used intact it does not create precipitated withdrawal symptoms due to the antagonist, but releases the agonist to treat pain. When NEOSD tablets are crushed, NEOSD will release a sufficient quantity of antagonist to block the euphoria effect of the agonist.

The NEOSD composition provides no significant release of the antagonist when the dosage form is administered to a subject intact. As used herein, no significant release refers to less than 20% of the antagonist released when the intact dosage form undergoes dissolution for 72 hours in 900 ml of purified water, using a paddle (USP apparatus II) at 100 rpm, e.g., less than 20%, 15%, 10%, 9%, 8%, 7%, 6%, 5%, 4%, 3%, 2%, 1%, 0.5%, or 0.1% of the antagonist released, e.g., 2% to 20% of the antagonist released. The lack of significant release occurs in dissolution medium of pH 1.2, pH 4.5, or pH 7.0, i.e., independently of pH. In one embodiment, the antagonist is naltrexone and less than 0.5 mg or 5% w/w is released over 72 hours when an intact tablet is taken orally, as measured in an in vitro dissolution study in 900 ml of purified water, using a paddle (USP apparatus II) at 100 rpm.

Amorphous polymers/viscoelastic polymers do not have any defined shape, or easily altered shape, like a liquid. Polymer chains with branches or irregular pendant groups cannot pack together regularly enough to form crystals. Amorphous regions of a polymer are made up of randomly coiled and entangled chains. They have been compared to a bucket containing a large number of entangled worms—each one 20-feet long and of ¼-inch thickness. The worms are so tangled that an entire worm cannot slide past the others, but small portions of the worms can twist around within the mass.

Amorphous polymers are softer than crystalline polymers and have lower melting points. The temperature and stress state have a profound effect on the molecular arrangement and hence the properties of a polymer. Under the action of sufficient stress, the polymer chains can uncoil and align over a period of time. At elevated temperatures, polymer chains have enough energy to rotate and coil up further.

The amorphous polymers used in the invention are inert, insoluble, non-swelling, have a very low moisture vapor transmission rate, lack hardening and provide solvent and chemical resistance. When heated or stress is applied, they change their rheological behaviors.

In certain embodiments, the tacky amorphous polymer is viscoelastic and is hydrophobic, non-gel forming, insoluble, and non-swelling in water, 0.1 N hydrochloric acid, pH 4.5 buffer, and pH 6.8 buffer. In some embodiments, the tacky amorphous polymer has a low glass transition temperature (Tg), e.g. of about −100° C. to about 150° C., e.g., about −100° C., −50° C., 0° C., 50° C., 100° C., or 150° C. or any range therein. In some embodiments, the tacky amorphous polymer has a moisture vapor transmission rate of less than 10 g/m$^2$/24 h as measured using 2.0 mm film using ASTM F1249, e.g., less than 10, 9, 8, 7, 6, 5, 4, 3, or 2 g/m$^2$/24 h. In some embodiments, the tacky amorphous polymer is in a semi-crystalline solid state. The molecular weight of the tacky amorphous polymer may be between about 2,500 and about 10,000,000 g/mol, e.g., about 2,500, 5,000, 10,000, 25,000, 50,000, 100,000, 250,000, 500,000, 750,000, 1,000,000, 2,000,000, 3,000,000, 4,000,000, 5,000,000, 6,000,000, 7,000,000, 8,000,00, 9,000,000, or 10,000,000 g/mol or any range therein.

In certain embodiments, the tacky amorphous polymer may be, without limitation, polysiloxane (e.g., silicone, e.g., 20,000 to 8,000,000 g/mol), polyisobutylene (e.g., 2500-6,000,000 g/mol), polyisoprene, polystyrene, polysulfone, copolymers thereof, or any combination thereof with molecular weight ranging from 10,000 to 4,000,000 g/mol.

The amount of the tacky amorphous polymer in each of the first particle and the second particle is from about 10% to about 75% w/w, e.g., about 20% to about 60% w/w, e.g., about 10%, 15%, 20%, 25%, 30%, 35%, 40%, 45%, 50%, 55%, 60%, 65%, 70%, or 75%, or any range therein. In some embodiments, the amount of the tacky amorphous polymer in each of the first particle and the second particle is the same. In some embodiments, the amount of the tacky amorphous polymer in each of the first particle and the second particle is different. For example, the second particle may have less or more of the tacky amorphous polymer than the first particle, e.g., 5%, 10%, 15%, 20%, 25%, 30%, 35%, 40%, 45%, or 50% less or more or any range therein.

The tacky amorphous polymer and the crystalline polymer curing agent arc present in a ratio suitable to decrease the tackiness of the amorphous polymer to the point that dosage forms can be prepared. In some embodiments, (he weight ratio of tacky amorphous polymer to crystalline polymer curing agent is from about 50:1 to about 1:50, e.g., about 50:1, 40:1, 30:1, 20:1, 10:1, 1:1, 1:10, 1:20, 1:30, 1:40, 1:50, or any range therein. In some embodiments, the ratio in each of the first particle and the second particle is the same. In some embodiments, the ratio in each of the first particle and the second particle is different.

In certain embodiments, the crystalline polymer curing agent is a water insoluble, non-film forming, crystalline polymer of natural or synthetic origin and is a solid at room temperature. In some embodiments, the crystalline polymer curing agent has a ring-and-ball softening point above 50° C., e.g., above 60° C., 70° C., or 80° C. In some embodiments, the particles comprise one or more crystalline polymer curing agents, e.g., 2, 3, or 4. Suitable crystalline polymer curing agents include, without limitation, terpene resin, polyvinyl acetate, or a combination thereof.

Terpene resins are pale amber, transparent, thermoplastic polyterpene hydrocarbon resins, of the type formula $(C_{10}H_{16})_n$. Depending on the nature of the end use, the terpene resins are supplied either in solid form or in solution in hydrocarbon solvents; the solid forms are made in a wide range of softening points or molecular weights. The commercially available polyterpene resins are produced with a variety of softening points (measured by the ASTM ring-and-ball method E28-51T), ranging from about 10° C. to 135° C., corresponding to a range from viscous liquid to hard, brittle solid polymers at ordinary temperatures. In certain embodiments of the present invention, the polyterpene has a molecular weight of about 1200 to 4000 g/mol, measured cryoscopically in benzene, a softening point above 70° C., and a melting point above 60° C.

Polyvinyl acetate is a colorless, nontoxic, insoluble thermoplastic resin prepared by the polymerization of vinyl acetate. It is used in the molecular weight range of about 15,000 to 150,000 g/mol.

The amount of the crystalline polymer curing agent in each of the first particle and the second particle is from about 5% to about 60% w/w, e.g., about 10% to about 40%, e.g., about 5%, 10%, 15%, 20%, 25%, 30%, 35%, 40%, 45%, 50%, 55%, or 60% or any range therein. In some embodiments, the amount of the crystalline polymer curing agent in each of the first particle and the second particle is the same. In some embodiments, the amount of the crystalline polymer curing agent in each of the first particle and the second particle is different. For example, the second particle may have less or more of the crystalline polymer curing agent than the first particle, e.g., 5%, 10%, 15%, 20%, 25%, 30%, 35%, 40%, 45%, or 50% less or more or any range therein.

In some embodiments, the ratio of crystalline polymer curing agent to tacky amorphous polymer is about 1:1 to about 15:1, e.g., about 1:1 to about 10:1, about 1:1 to about 8:1, e.g., about 1:1 to about 5:1.

The channelizer may be any agent that is suitable to draw water or another solvent into the first particle to enhance dissolution of the agonist. The channelizers either dissolve themselves (if they are soluble) or direct the solution (if they are insoluble), like dissolution media, through the hydrophobic impermeable amorphous polymer to the agonist for its release. If the channelizer is not added, then the formulation will not release any agonist. Antagonist particles do not have the channelizer, so the dissolution media cannot penetrate and does not release the antagonist drug, so the antagonist part is sequestered in the NEOSD dosage form.

Suitable channelizers include, without limitation, electrolytes (e.g., sodium chloride and the like), soluble excipients, dye and insoluble excipients, talc, colloidal silicon dioxide, zinc stearate, magnesium stearate, powdered sugar, lactose, titanium dioxide, aluminum oxide, synthetic wax, carnauba wax, bees wax, paraffin wax, or any combination thereof. In certain embodiments, there may two or more channelizers, such as colloidal silicon dioxide and talc.

The amount of channelizer in the particle may be about 0.1% to about 25% w/w, e.g., about 1%, to about 15%, e.g., 0.1%, 0.5%, 1%, 5%, 10%, 15%, 20%, or 25%, or any range therein. In some embodiments, the channelizer may be present in a ratio to the amorphous polymer of about 1:20 to about 1:70 w/w, e.g., about 1:20, 1:30, 1:40,1:50, 1:60, or 1:70 w/w.

Figure 2:
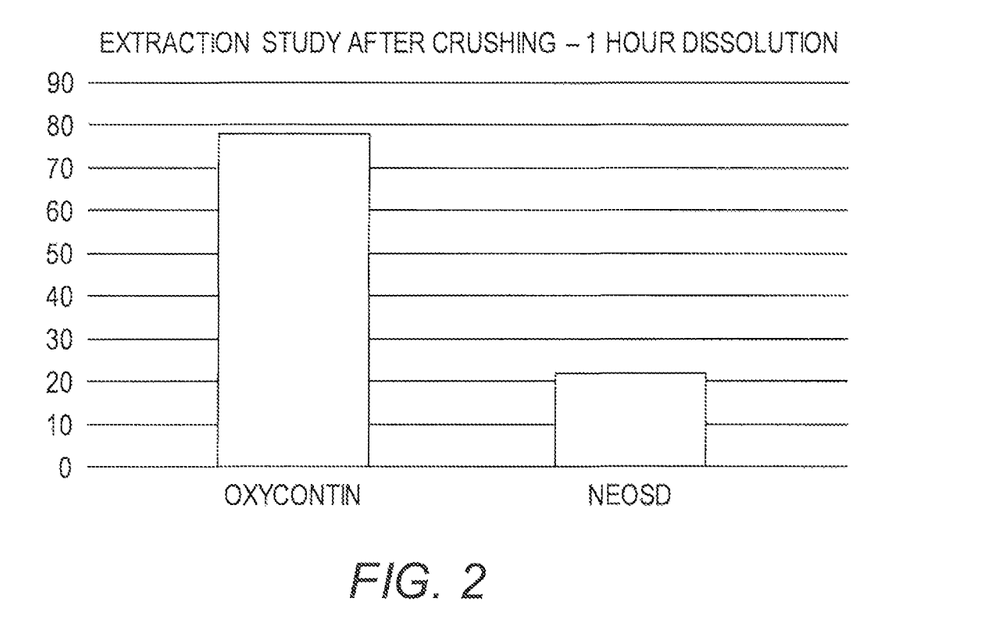
FIG. 2 shows an extraction study of crushed tablets with 1 hour dissolution.

The presence of the channelizer with the amorphous polymer when NEOSD extended release oxycodone hydrochloride 40 mg tablets are crushed by a pill crusher and a dissolution assay was performed (USP II paddle assay in 900 ml purified water for 60 minutes) on the crushed tablets, it showed little dissolution (FIG. 2). The tablet formulation is shown in Table 6. In contrast, the same assay was applied to marketed OXYCONTIN® 40 mg tablets and the dissolution showed marked extraction of the oxycodone hydrochloride drug (FIG. 2). The data show clearly that the extraction of NEOSD tablets after being crushed in a pill crusher showed much less drug release compared to the marketed OXYCONTIN® 40 mg tablets. This shows it is difficult to extract the drug from NEOSD dosage forms by physically tampering with the tablets. The channelizer is a very fine insoluble crystalline particle, which serves to channelize the dissolution medium or water into the drug covered polymer. When the tablet gets crushed, as it is crystalline in nature, the channelizer is squeezed inside of the tacky amorphous polymer, so less channels are available, thereby less dissolution medium will reach the drug for dissolution and it extracts less drug when the NEOSD tablet is crushed.

TABLE 6

| Ingredient | mg/tablet | grams/batch of 1000 tabs |
| --- | --- | --- |
| Oxycodone Hydrochloride | 20 | 20 |
| Naltrexone Hydrochloride | 6 | 6 |
| Polyisobutylene | 52.8 | 52.8 |
| Polyvinyl Acetate | 66 | 66 |
| Colloidal silicon dioxide | 0.2 | 0.2 |
| Talc | 4 | 4 |
| Mineral oil | 4 | 4 |
| Stearic acid | 9 | 9 |

The tackifying agent may be any agent that causes the amorphous polymer to regain its tackiness (e.g., modulate the viscoelastic properties of the amorphous polymer). The tackifying agent may be an agent that dissolves in the amorphous polymer and softens and makes the agonist particle non-releasable and the antagonist particle sequestered by making the amorphous polymer in the agonist and antagonist particles stick together. The tackifying agent, along with the API, tacky amorphous polymer and crystalline polymer curing agent, forms a tacky and hard tablet. The effect of the tackifying agent on the amorphous polymer is important as it modifies or alters the rheological properties and bring back the tackiness of the amorphous polymer in a controlled manner. After regaining the tackiness or stickiness of the amorphous polymer, this oral solid dosage form becomes non-extractable by physical tempering and solvent extraction.

Suitable tackifying agents include, but are not limited to, mineral oil, shellac, polyethylene glycol 200, polyethylene glycol 300, polyethylene glycol 400, polyethylene glycol 540, polyethylene glycol 600, polyethylene glycol 1000, polyethylene glycol 1450, polyethylene glycol 3350, polyethylene glycol 4000, polyethylene glycol 4600, polyethylene glycol 8000, silicone oil, or any combination thereof.

The amount of tackifying agent in the particle may be about 0.25% to about 20% w/w, e.g., about 1%, to about 10%, e.g., 0.1%, 0.5%, 1%, 5%, 10%, 15%, or 20%, or any range therein. In some embodiments, the amount of the tackifying agent in each of the first particle and the second particle is the same. In some embodiments, the amount of the tackifying agent in each of the first particle and the second particle is different. For example, the second particle may have less or more of the tackifying agent than the first particle, e.g., 5%, 10%, 15%, 20%, 25%, 30%, 35%, 40%, 45%, or 50% less or more or any range therein. In one embodiment, second particle comprises at least 15% more, e.g., at least 25% more, tackifying agent w/w than the first particle.

In certain embodiments, the dosage form may comprise a sensory agent as a further abuse deterrent. The sensory agent will modify the psychological and/or sensory perception of the dosage form by a subject when the dosage form is physically altered. The sensory agent may be any agent that provides an unpleasant sense, e.g., bitterness, heat, or bad taste.

In some embodiments, the sensory agent is benzonatate, capsaicin, bittering agent, or any combination thereof. In some embodiments, the sensory agent is capsaicin or a derivative thereof. The capsaicin or a derivative thereof (e.g., capsaicinoids), may be present in a suitable amount to prevent ingestion, e.g., about 10,000 to 12.0 million Scoville heat units per dosage form, e.g., at least about 10,000, 50,000, 100,000, 500,000, or 1 million Scoville heat units per dosage form.

In some embodiments, substantially no sensory agent is released from the dosage form when it is administered intact, e.g., less than about 20%, 15%, 10%, 5%, 4%, 3%, 2%, 1%, 0.5%, or 0.1%. In some embodiments, the sensory agent is capsaicin and substantially no capsaicin is released during dissolution of the dosage form in 40% alcohol in 0.1 N HCl at 50 RPM for 2 hours. In certain embodiments, the oral dosage form does not significantly release any sensory agent for at least about 12 to 24 hours after oral administration, e.g., at least about 6, 12, 18, 24, 30, 36, 52, or 48 hours after oral administration.

In some embodiments, the majority of the sensory agent is released from the dosage form when it is tampered with, e.g., ground up. In some embodiments, at least about 50%, 60%, 70%, 80%, or 90% of the sensory agent is released upon tampering with the dosage form. In one embodiment, at least about 70% of capsaicin is released from the dosage form during dissolution of the dosage form in 40% alcohol in 0.1 N HCl at 50 RPM for 2 hours when the dosage form is ground prior to dissolution.

The sensory agent may be present in an amount of about 0.1 mg to 15 mg per dosage form, e.g., about 0.1, 0.5, 1.2, 3, 4, 5, 6, 7, 8, 9, 10, 11, 12, 13, 14, or 15 mg or any range therein.

In some embodiments, the sensory agent cannot be separated, isolated, or removed from the dosage form. In some embodiments, the sensory agent is present in the dosage form as part of a third particle. In certain embodiments, the third particle may comprise:
  i) a tacky amorphous polymer;
  ii) a crystalline polymer curing agent for the amorphous polymer; and
  iii) a softener.

In some embodiments, the dosage form or the particles within the dosage form may further comprise a lubricant. Any suitable lubricant may be used. Examples include, without limitation, stearic acid, polyethylene glycol 8000, or a combination thereof.

The amount of the lubricant in each of the first particle and the second particle may be from about 0.5 to about 15% w/w, e.g., about 0.5%, 1%, 5%, 10%, or 15%, or any range therein.

In some embodiments, the non-extractable oral solid dosage form comprises, consists essentially of, or consists of two different particles.
the first particle comprising, consisting essentially of, or consisting of:
  i) about 5% to about 60% tacky amorphous polymer;
  ii) about 10% to about 75% crystalline polymer curing agent for the amorphous polymer;
  iii) about 1% to about 35% agonist active pharmaceutical ingredient;
  iv) about 0.1% to about 15% channelizer; and
  v) about 0.1% to about 20% tackifying agent;
the second particle comprising, consisting essentially of, or consisting of:
  i) about 5% to about 75% tacky amorphous polymer;
  ii) about 10% to about 55% crystalline polymer curing agent for the amorphous polymer;
  iii) about 3% to about 50% antagonist to the active pharmaceutical ingredient;
  iv) about 0% to about 5% channelizer; and
  v) about 0.1% to about 35% tackifying agent;
the dosage form further comprising about 1% to about 20% lubricant.

In some embodiments, the non-extractable oral solid dosage form comprises, consists essentially of, or consists of two different particles.
the first particle comprising, consisting essentially of, or consisting of:
  i) polyisobutylene or polysulfone as the tacky amorphous polymer;
  ii) polyvinyl acetate or terpene resin as the crystalline polymer curing agent for the amorphous polymer;
  iii) agonist active pharmaceutical ingredient;
  iv) talc, colloidal silicon dioxide, or carnauba wax as the channelizer; and
  v) mineral oil, polyethylene glycol, or shellac as the tackifying agent;
the second particle comprising, consisting essentially of, or consisting of:
  i) polyisobutylene or polysulfone as the tacky amorphous polymer;
  ii) polyvinyl acetate or terpene resin as the crystalline polymer curing agent for the amorphous polymer;
  iii) about 1% to about 50% antagonist to the active pharmaceutical ingredient;
  iv) talc, colloidal silicon dioxide, or carnauba wax as the optional channelizer; and
  v) mineral oil, polyethylene glycol, or shellac as the tackifying agent; the dosage form further comprising stearic acid as the lubricant.

In some embodiments, the non-extractable oral solid dosage form comprises, consists essentially of, or consists of two different particles,
the first particle comprising, consisting essentially of, or consisting of:
  i) about 5% to about 60% polyisobutylene or polysulfone as the tacky amorphous polymer:
  ii) about 10% to about 75% polyvinyl acetate or terpene resin as the crystalline polymer curing agent for the amorphous polymer;
  iii) about 1% to about 35% agonist active pharmaceutical ingredient;
  iv) about 0.1% to about 15% talc, colloidal silicon dioxide, or carnauba wax channelizer; and
  v) about 0.1% to about 20% mineral oil, polyethylene glycol, or shellac as the tackifying agent;
the second particle comprising, consisting essentially of, or consisting of:
  i) about 5% to about 75% polyisobutylene or polysulfone as the tacky amorphous polymer;
  ii) about 10% to about 55% polyvinyl acetate or terpene resin as the crystalline polymer curing agent for the amorphous polymer;
  iii) about 1% to about 50% antagonist to the active pharmaceutical ingredient;
  iv) about 0% to about 5% talc, colloidal silicon dioxide, or carnauba wax channelizer; and
  v) about 0.1% to about 35% mineral oil, polyethylene glycol, or shellac as the tackifying agent;
the dosage form farther comprising about 1% to about 20% stearic acid.

The non-extractable oral solid dosage forms of the invention deter potential abusers. In some embodiments, when the dosage form is tampered with, the agonist and antagonist are released together. In additional embodiments, when the dosage form is heated, e.g., when placed in a spoon and the spoon is heated by flame, the dosage form docs not form a liquid that can be administered, such as by a syringe. Additionally, when heated, the dosage form does not provide any smoke or vapor for inhalation.

One aspect of the invention relates to methods of preparing the non-extractable oral solid dosage forms of the invention. The dosage forms may be prepared by any suitable method known in the art. Suitable methods include, without limitation, a hot-melt process, hot-melt extrusion, or an injection molding process. In one embodiment, the dosage form is produced by a hot-melt process.

In general, each particle may be prepared separately by healing the tacky amorphous polymer, adding the active agent and mixing, then adding the additional components to produce a non-tacky and free flowing mixture, and then forming the particles. The particles are then cured such that the amorphous polymer becomes re-tackified. Depending on the type of dosage from being prepared, the particles may be combined in a suitable manner and cured at the appropriate stage. In the embodiment of a capsule dosage form, the particles may be mixed, cured, and placed in capsules. In the embodiment of a matrix tablet, the particles may be mixed, compressed into tablets, and then cured. In the embodiment of a multilayer tablet, each type of particle may be compressed into desired form, the forms compressed together into a tablet, and then cured.

In one embodiment, the NEOSD antagonist granules are made with the above process and further fluid bed coated with hydrophobic polymers to make the antagonist sequestered. Suitable hydrophobic polymers include, without limitation, ethylcellulose, polyvinyl acetate, polymethacrylic acid copolymers, shellac, and zein polymers. In one embodiment, the hydrophobic polymer is shellac, as it does not form a typical color variation with the antagonist granules.

In one embodiment, the antagonist granules are prepared by the above method and are filled in capsules containing a sequestered antagonist and releasable agonist granules.

In one embodiment, the above granules are compressed into bi-layer tablets, containing one layer of antagonist and another layer of agonist, and subsequently coated with an elegant coating using, e.g., Opadry II.

In one embodiment, the NEOSD is manufactured after melting the polymers and adding the drug (agonist and antagonist) separately and extruding along with the channelizer, then spheronized to form antagonist granules and agonist granules.

In one embodiment, the NEOSD is manufactured by injection molding, where the amorphous polymer/crystalline polymer along with channelizer and agonist/antagonist is melted and injected into a tablet shape mold at part of a single layer or bi-layer molded tablet.

In one embodiment for forming a matrix tablet, a method of producing the non-extractable oral solid dosage form of the invention comprises:
a) preparing a first particle by:
   i) heating the tacky amorphous polymer above 80° C.;
   ii) adding the agonist and mixing;
   iii) adding the channelizer, crystalline polymer curing agent, and tackifying agent to produce a non-tacky and free flowing mixture; and
   iv) milling and blending the mixture;
b) preparing a second particle by:
   i) heating the tacky amorphous polymer above 80° C.;
   ii) adding the antagonist and mixing;
   iii) adding the crystalline polymer curing agent and tackifying agent to produce a non-tacky and free flowing mixture; and
   iv) milling and blending the mixture;
c) combining the first and second particle into a mixture;
d) compressing the mixture: and
e) curing the mixture, wherein the amorphous polymer becomes re-tackified.

The curing conditions may be any conditions suitable for re-tackifying the amorphous polymer. In some embodiments, the curing time is from about 1 hour to about 102 hours, e.g., about 3 hours to about 65 hours, e.g., about 1, 2, 3, 4, 5, 10, 15, 20, 25, 30, 35, 40, 45, 50, 55, 60, 65, 70, 75, 80, 85, 90, 95, or 100 hours or any range therein.

In some embodiments, the curing temperature is about 30° C. degrees to about 90° C., e.g., about 35° C. to about 65° C., e.g., about 40° C. to about 60° C., e.g., about 30° C., 35° C., 40° C., 45° C., 50° C., 55° C., 60° C., 65° C., 70° C., 75° C., 80° C. 85° C., or 90° C. or any range therein.

In certain embodiments, the process of making the NEOSD is hot-melt process as follows. To make the first particle, tacky amorphous polymer, crystalline polymer curing agent, channelizer, tackifying agent, and crystalline drug opioid/API are heated above 50° C. in a jacketed high shear mixer and after forming a uniform melted blend, the hot melted suspension is cooled in a cooling belt, where the suspension is cooled below 10° C., and the cooled non tacky mass is milled using a suitable Fitzmill fitted with a suitable screen. To make the second particle, tacky amorphous polymer, crystalline polymer curing agent, tackifying agent, and antagonist are healed above 50° C. in a jacketed high shear mixer and after forming a uniform melted blend, the hot melted suspension is cooled in a cooling belt, where the suspension is cooled below 10° C., and the cooled non tacky mass is milled using a suitable Fitzmill fitted with a suitable screen.

The first and second particles are blended together, lubricated and compressed into tablets. The compressed tablets arc then cured above 25° C. for a few minutes to about 100 hours and optionally film coated for appearance.

In specific embodiments, when the amorphous polymer, which is very tacky, is heated along with crystalline drug, the viscosity of the amorphous polymer becomes very watery and forms an insoluble barrier surrounding the drug which has the abuse potential, to which is added the channelizer, which directs the water or dissolution media through the insoluble barrier to the drug for its dissolution. The curing agent and the tackifying agent are added. After cooling, the mass become non-tacky and hard. At this stage it can be milled into free flowing granules, which are lubricated during the regular blending process and compressed into a tablets.

In specific embodiments, after compression the tablets arc cured by heat, which makes the amorphous pan of the agonist and antagonist particles tacky. This happens in presence of tackifying agent and heat. The melted tackifying agent softens and dissolves part of the amorphous polymer and makes it very tacky or sticky. This process closes the open part of the antagonist granule created during the milling, making the antagonist non-releasable and impossible to isolate or separate antagonist from agonist.

In some embodiments, the particles and/or the dosage forms may be coated, e.g., with a sustained-release coating, controlled-release coating, or delayed-release coating. Such coatings are particularly useful when the dosage form comprises an opioid antagonist in non-releasable form. The coatings may include a sufficient amount of a hydrophobic material to obtain a weight gain level from about 5% to about 60% to make the antagonist a non-releasable form.

Another aspect of the invention relates to methods of administering an agonist active pharmaceutical ingredient to a subject in need thereof, comprising administering the non-extractable oral solid dosage form of the invention to the subject. The dosage form may be administered in therapeutically or prophylactically effective amounts.

In some embodiments, the agonist is an opioid and the subject is in need of treatment with an opioid, e.g., for treating pain.

The dosage forms according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder or symptom that would benefit from the delivery of the dosage form of the invention. As a further option, the subject can be a laboratory animal and/or an animal model of disease.

Having described the present invention, the same will be explained in greater detail in the following examples, which are included herein for illustration purposes only, and which are not intended to be limiting to the invention.

EXAMPLE 1

A 20 mg oxycodone formulation (Table 7) was prepared using polyisobutylene as the amorphous polymer and polyvinyl acetate as the curing agent.

TABLE 7

| Ingredient | mg/tablet | grams/batch of 1000 tabs |
|---|---|---|
| Oxycodone Hydrochloride | 20 | 20 |
| Naltrexone Hydrochloride | 10 | 10 |
| Polyisobutylene | 38.8 | 38.8 |
| Polyvinyl Acetate | 106 | 106 |
| Colloidal silicon dioxide | 0.2 | 0.2 |
| Talc | 4 | 4 |
| Mineral oil | 4 | 4 |
| Stearic acid | 7 | 7 |

The tablets were prepared by the following procedure.
Antagonist Granulation:
1. Polyisobutylene was heated above 50° C. in a jacketed vessel and mineral oil added.
2. When the polyisobutylene completely melted the colloidal silicon dioxide was added and stirred for 10 minutes.
3. Naltrexone HCl was added to the above blend and mixed for 10 minutes.
4. Polyvinyl acetate was added next and the temperature was maintained above 40° C. with stirring for 20 minutes until it formed a homogenous suspension.
5. The above suspension was poured into a cooling chiller belt maintained below 10° C.
6. After cooling, the mass was milled using a Fitz-mill at knives forward.

Agonist Granulation:
7. Steps 1 and 2 were repeated and oxycodone HCl API was added to the above blend and mixed for 10 minutes.
8. Steps 4 to 6 were followed.
9. The milled granules were then blended together along with talc and lubricated using stearic acid.
10. The final granules were compressed into tablets using a Rimek Mini II R&D scale compression machine and cured at 30° C.
11. The cured tablets were film coated for elegance.

EXAMPLE 2

A 20 mg oxycodone formulation (Table 8) was prepared without the tackifying agent in NEOSD tablets.

TABLE 8

| Ingredient | mg/tablet | grams/batch of 1000 tabs |
|---|---|---|
| Oxycodone hydrochloride | 20 | 20 |
| Naltrexone hydrochloride | 10 | 10 |
| Polyisobutylene | 38.8 | 38.8 |
| Polyvinyl Acetate | 106 | 106 |
| Colloidal silicon dioxide | 0.2 | 0.2 |
| Talc | 4 | 4 |
| Stearic acid | 7 | 7 |

The tablets were prepared by the following procedure.
Antagonist Granulation:
1. Polyisobutylene was heated above 50° C. in a jacketed vessel.
2. When the polyisobutylene was completely melted the colloidal silicon dioxide was and stirred for 10 minutes.
3. Naltrexone HCl was added to the above blend and mixed for 10 minutes.
4. Polyvinyl acetate was added next and the temperature was maintained above 40° C. with stirring for 20 minutes until it formed a homogenous suspension.
5. The above suspension was poured into a cooling chiller belt maintained below 10° C.
6. After cooling, the mass was milled using a Fitz-mill at knives forward.

Agonist Granulation:
7. Steps 1 and 2 were repeated and oxycodone HCl API was added to the above blend and mixed for 10 minutes.
8. Steps 4 to 6 are followed
9. The milled granules were then blended together along with talc and lubricated using stearic acid.
10. The final granules were compressed into tablets using a Rimek Mini II R&D scale compression machine and cured at 30° C.
11. The cured tablets were film coated for elegance.

Figure 3:
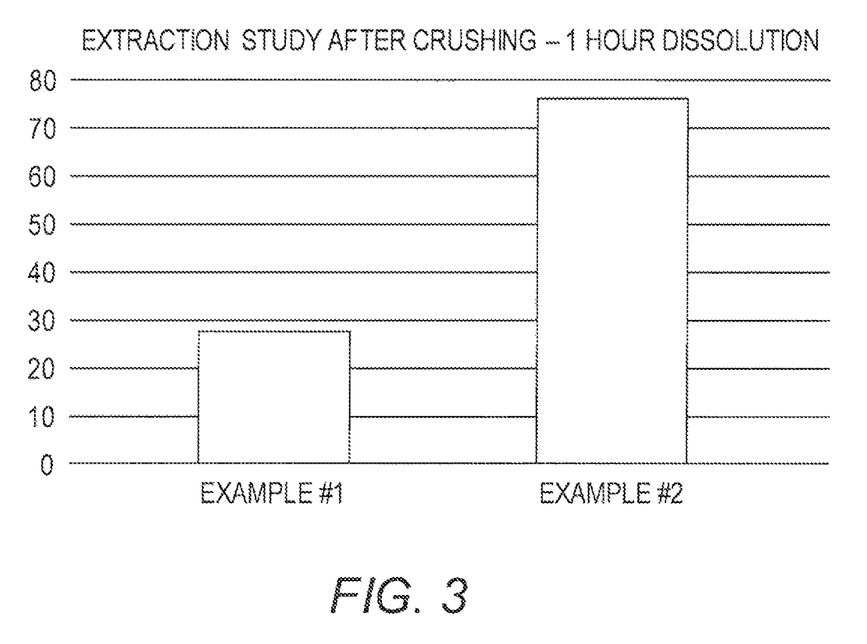
FIG. 3 shows an extraction study of crushed tablets with 1 hour dissolution.

The Example 1 and Example 2 tablets were crushed using a pill crusher and the crushed tablets were subjected to dissolution at the following settings: Paddle (USP apparatus II) @50 rpm, using 900 ml, of Purified water at 37° C.+/−0.5° C., pulled the samples al the end of one hour, the samples were tested using a HPLC test method. The results are shown in FIG. 3. The data from the dissolution test shows that the tablets from Example 1 release less drug compared to the tablets from Example 2, demonstrating that the presence of the tackifying agent makes this NEOSD a non-extractable dosage form.

EXAMPLE 3

A 20 mg oxycodone formulation (Table 9) is prepared using polysulfone amorphous polymer and polyvinyl acetate as a curing agent.

TABLE 9

| Ingredient | mg/tablet | grams/batch of 1000 tabs |
|---|---|---|
| Oxycodone hydrochloride | 10 | 10 |
| Naltrexone hydrochloride | 3 | 3 |
| Polysulfone | 45.5 | 45.5 |
| Polyvinyl Acetate | 105.3 | 105.3 |
| Colloidal silicon dioxide | 0.2 | 0.2 |
| Carnauba wax | 2 | 2 |
| Mineral oil | 3 | 3 |
| Stearic acid | 12 | 12 |

The tablets arc prepared by the following procedure.
Antagonist Granulation:
1. Polysulfone is healed above 50° C. in a jacketed vessel.
2. When the polyisobutylene completely melts the colloidal silicon dioxide is added and stirred for 10 minute.
3. Naltrexone HCl is added to the above blend and mixed for 10 minutes.
4. Polyvinyl acetate is added next and the temperature is maintained above 40° C. with stirring for 20 minutes until it forms a homogenous suspension.
5. The above suspension is poured into a cooling chiller belt maintained below 10° C.
6. After cooling, the mass is milled using a Fitz-mill at knives forward.

Agonist Granulation:
7. Steps 1 and 2 are repeated and oxycodone HCl API is added to the above blend and mixed for 10 minutes.
8. Steps 4 to 6 are followed.
9. The milled granules are then blended together along with tale and lubricated using stearic acid.

10. The final granules are compressed into tablets using a Rimek Mini II R&D scale compression machine and cured at 30° C.
11. The cured tablets are film coated for elegance.

The release of naltrexone is determined by dissolution testing conducted according to USP Chapter <711>. The test uses USP Apparatus II (Paddles) at 100 rpm, 900 mL of water, 37° C. Samples are drawn at 72 hours and assayed by a HPLC assay procedure.

The release of oxycodone is determined by dissolution testing conducted according to USP Chapter <711>. The test uses USP Apparatus II (Paddles) at 50 rpm, 900 mL of water, 37° C. Samples are drawn at 12 hours and assayed by a HPLC assay procedure. Limit: not less than 85% release at 12 hours.

Intact tablets show naltrexone release 5.1% at 72 hours of dissolution and oxycodone meets the above dissolution requirements.

The tablets are crushed in a coffee grinder and subjected to dissolution testing with the above parameters for 1 hour of dissolution. The crushed tablets release 89% of the naltrexone.

The data demonstrate that if the tablets is taken intact, they release less than 5.1%, which is 0.153 mg of naltrexone over a period of 72 hours, indicating sequestration, but when the tablets are powdered using a coffee grinder, they showed release of 2.67 mg of naltrexone, which will interfere with the agonist actions of oxycodone and euphoria will be prevented.

EXAMPLE 4

A 10 mg oxymorphone extended release formulation (Table 10) was prepared using polyisobutylene amorphous polymer and terpene resin as a curing agent as capsules.

TABLE 10

| Ingredient | mg/capsule | grams/batch of 1000 capsules |
| --- | --- | --- |
| Oxymorphone HCl | 10 | 20 |
| Naltrexone HCl | 6 | 60 |
| Polyisobutylene | 68 | 28.9 |
| Terpene resin | 90.6 | 90.6 |
| Colloidal silicon dioxide | 0.5 | 0.5 |
| Talc | 8 | 8 |
| Mineral oil | 2 | 5 |
| Polyethylene glycol 6000 | 10 | 10 |
| Shellac Ammonium salt | 10 | 10 |
| Triethyl citrate | 1 | 1 |

The capsules were prepared by the following procedure.
Antagonist Granulation:
1. Polyisobutylene was heated above 50° C. in a jacketed vessel.
2. When the polyisobutylene completely melted the colloidal silicon dioxide was added and stirred for 10 minutes.
3. Naltrexone HCl was added to the above blend and mixed for 10 minutes.
4. Terpene resin was added next and the temperature was maintained above 40° C. with stirring for 20 minutes until it formed a homogenous suspension.
5. The above suspension was poured into a cooling chiller belt maintained below
6. After cooling, the mass was milled using a Fitz-mill at knives forward.
Antagonist Granules Coating:
7. Shellac ammonium salt is dispersed in water followed by addition of diethyl citrate as plasticizer.
8. The naltrexone antagonist granules were coated using a fluid bed coater fitter with Wurster column with the shellac aqueous solution.
Agonist Granules:
9. Polyisobutylene was heated above 50° C. in a jacketed vessel.
10. When the polyisobutylene completely melted the colloidal silicon dioxide was added and stirred for 10 minutes.
11. Oxymorphone HCl was added to the above blend and mixed for 10 minutes.
12. Terpene resin was added next and the temperature was maintained above 40° C. with stirring for 20 minutes until it formed a homogenous suspension.
13. The above suspension was poured into a cooling chiller belt maintained below 10° C.
15. After cooling, the mass was milled using a Fitz-mill at knives forward.
16. The naltrexone antagonist part and the oxymorphone agonist part granules were blended together with talc and polyethylene glycol as lubricant and filled in a capsule.

The release of naltrexone was determined by dissolution testing conducted according to USP Chapter <711>. The test used USP Apparatus II (Paddles) at 100 rpm, 900 mL of water, 37° C. Samples were drawn at 72 hours and assayed by a HPLC assay procedure.

The release of oxymorphone HCl was determined by dissolution testing conducted according to USP Chapter <711>. The test used USP Apparatus II (Paddles) at 50 rpm, 900 mL of water, 37° C. Samples were drawn at 12 hours and assayed by a HPLC assay procedure. Limit: not less than 85% release at 12 hours.

Intact tablets showed naltrexone release of 1.92% at 72 hours of dissolution and oxymorphone met the above release criteria.

With this formulation the naltrexone granules cannot be separated or isolated as there is no difference in the color of the naltrexone HCl granules and the oxymorphone HCl granules, due to the shellac coating. If other hydrophobic coating materials like ethylcellulose or polymethacrylate co-polymers were used it will show as white to off white naltrexone granules, which can be isolated from the oxymorphone granules.

The dissolution data of the naltrexone drug release showed release of 0.1152 grams of naltrexone over a period of 72 hours, which is considered sequestration. When used as intact capsules, it will release normally the oxymorphone HCl to treat pain, but when it is crushed by a coffee grinder or chewed to get high from drug abuse, it will release substantial amounts of naltrexone and act as an antagonist and prevent the drug abuse.

EXAMPLE 5

A 20 mg hydrocodone bitartrate formulation (Table 11) was prepared using polyisobutylene amorphous polymer and terpene resin as a curing agent with capsaicin as a sensory agent.

TABLE 11

| Ingredient | mg/tablet | grams/batch of 1000 tabs |
| --- | --- | --- |
| Hydrocodone Bitartrate | 20 | 20 |
| Polyisobutylene | 109.9 | 109.9 |
| Terpene resin | 110.6 | 90.6 |
| Colloidal silicon dioxide | 0.5 | 0.5 |

TABLE 11-continued

| Ingredient | mg/tablet | grams/batch of 1000 tabs |
|---|---|---|
| Talc | 8 | 8 |
| Mineral oil | 5 | 5 |
| Stearic acid | 10 | 10 |
| FD&C Red #40 | 2 | 2 |
| Capsaicin resin 2,000,000 SHU | Qty for 2.0 million SHU units | Qty for 2.0 million SHU units |

The tablets were prepared by the following procedure.
1. Polyisobutylene and mineral oil was heated above 50° C. in a jacketed vessel.
2. When the polyisobutylene completely melted the colloidal silicon dioxide was added.
3. Hydrocodone bitartrate was added to the above blend and mixed for 10 minutes.
4. Holy terpene was added and the temperature was maintained above 40° C. with stirring for 20 minutes until it formed a homogenous suspension.
5. The above suspension was poured into a cooling chiller belt maintained below 10° C.
8. After 30 minutes of cooling, the mass was milled using a Fitzmill at knives forward setting using a sieve equivalent to 14 mesh.

Capsaicin Granules:
9. Polyisobutylene and mineral oil was heated above 50° C. in a jacketed vessel.
10. When the polyisobutylene completely melted the colloidal silicon dioxide was added.
11. Capsaicin was added to the above and melted together and after forming a homogenous paste, terpene resin was added and the mass poured into a cooling belt and the cooled compacts were milled in a Fitzmill.
12. The milled granules of hydrocodone bitartrate granules and the capsaicin granules were blended and then lubricated using stearic acid.
13. The final granules were compressed into tablets using a Rimek Mini II R&D scale compression machine and cured at 30° C.

The release of hydrocodone bitartrate and capsaicin was determined by dissolution testing conducted according to USP Chapter <711>. The test used USP Apparatus II (Paddles) at 50 rpm, 900 mL of water, 37° C. Samples were drawn at 12 hours and assayed by a HPLC assay procedure. Limit: not less than 85% release of hydrocodone bitartrate at 12 hours.

The results showed that hydrocodone bitartrate dissolution met the above expectations and capsaicin did not show any release at 1 hour.

The results demonstrated that when the hydrocodone bitartrate tablets are taken as intact it will release the hydrocodone drug and the capsaicin will remain in the tablets as sequestered.

If the above tablets are crushed using a coffee grinder or chewed it will release the capsaicin. Habanera peppers have SHU units of 200,000 to 500,000, with 2.0 million SHU units, it will be very fiery and one cannot take it and it will make one spit out the chewed or crushed tablets.

The foregoing is illustrative of the present invention, and is not to be construed as limiting thereof. The invention is defined by the following claims, with equivalents of the claims to be included therein.

I claim:

1. A non-extractable oral solid dosage form comprising two different particles, the first particle comprising:
   i) a tacky amorphous polymer selected from the group consisting of polyisobutylene, polyisoprene, polysulfone, copolymers thereof, and combinations thereof;
   ii) a crystalline polymer curing agent for the amorphous polymer which is terpene resin;
   iii) an agonist active pharmaceutical ingredient;
   iv) a channelizer selected from the group consisting of talc, colloidal silicon dioxide, zinc stearate, magnesium stearate, powdered sugar, lactose, titanium dioxide, aluminum oxide, and combinations thereof; and
   v) a tackifying agent selected from the group consisting of mineral oil, shellac, silicone oil, and combinations thereof;

the second particle comprising:
   i) a tacky amorphous polymer selected from the group consisting of polyisobutylene, polyisoprene, polystilfone, copolymers thereof, and combinations thereof;
   ii) a crystalline polymer curing agent for the amorphous polymer which is terpene resin;
   iii) an antagonist to the active pharmaceutical ingredient;
   iv) optionally a channelizer selected from the group consisting of talc, colloidal silicon dioxide, zinc stearate, magnesium stearate, powdered sugar, lactose, titanium dioxide, aluminum oxide, and combinations thereof; and
   v) a tackifying agent selected from the group consisting of mineral oil, shellac, silicone oil, and combinations thereof;

wherein the agonist is releasable and the antagonist is substantially non-releasable upon oral administration of the dosage form.

2. The non-extractable oral solid dosage form of claim 1, wherein the dosage form is a tablet, capsule, microcapsule, granule, pellet, lollipop, or lozenge.

3. The non-extractable oral solid dosage form of claim 1, wherein the dosage form is a tablet.

4. The non-extractable oral solid dosage form of claim 3, wherein the tablet is a matrix tablet in which the first and second particles are intermingled uniformly.

5. The non-extractable oral solid dosage form of claim 1, wherein the amount of agonist in the first particle is about 0.1% to about 30% w/w.

6. The non-extractable oral solid dosage form of claim 1, wherein the agonist is a central nervous stimulant, opioid, barbiturate, benzodiazepine, or sedative.

7. The non-extractable oral solid dosage form of claim 1, wherein the agonist is opioid and the antagonist is an opioid antagonist.

8. The non-extractable oral solid dosage form of claim 1, wherein the antagonist is naloxone, nalmefene, or naltrexone.

9. The non-extractable oral solid dosage form of claim 1, comprising about 0.25 mg to about 5.0 mg of antagonist, per 5 mg of agonist.

10. The non-extractable oral solid dosage form of claim 1, wherein the weight ratio of tacky amorphous polymer to crystalline polymer curing agent is from about 50:1 to about 1:50.

11. The non-extractable oral solid dosage form of claim 1, wherein the amount of the tacky amorphous polymer in each of the first particle and the second particle is from about 10% to about 75% w/w.

12. The non-extractable oral solid dosage form of claim 1, wherein the amount of the crystalline polymer curing agent in each of the first particle and the second particle is from about 5% to about 60% w/w.

13. The non-extractable oral solid dosage form of claim 1, wherein the amount of the channelizer in the first particle is from about 0.1% to about 25% w/w.

14. The non-extractable oral solid dosage form of claim 1, wherein the amount of the tackifying agent in each of the first particle and the second particle is from about 0.25% to about 20% w/w.

15. The non-extractable oral solid dosage form of claim 1, wherein the second particle comprises at least 15% more tackifying agent w/w than the first particle.

16. The non-extractable oral solid dosage form of claim 1, further comprising a sensory agent which will modify psychological and sensory perception of the dosage form when the dosage form is physically altered.

17. The non-extractable oral solid dosage form of claim 16, wherein the sensory agent is benzonatate, capsaicin, bittering agent, or any combination thereof.

18. The non-extractable oral solid dosage form of claim 16, wherein the sensory agent is present in an amount of about 0.1 mg to 15 mg per dosage form.

19. The non-extractable oral solid dosage form of claim 16, wherein the sensory agent is part of a third particle comprising:
   i) a tacky amorphous polymer selected from the group consisting of polyisobutylene, polyisoprene, polystyrene, polysulfone, copolymers thereof, and combinations thereof; and
   ii) a crystalline polymer curing agent for the amorphous polymer which is terpene resin.

20. The non-extractable oral solid dosage form of claim 1, further comprising a lubricant.

21. The non-extractable oral solid dosage form of claim 20, wherein the lubricant is stearic acid.

22. The non-extractable oral solid dosage form of claim 20, wherein the amount of the lubricant in each of the first particle and the second particle is from about 0,5 to about 15% w/w.

23. The non-extractable oral solid dosage form of claim 1, wherein the dosage form provides immediate release of the agonist.

24. The non-extractable oral solid dosage form of claim 1, wherein the dosage form provides controlled release of the agonist.

25. The non-extractable oral solid dosage form of claim 1, wherein the first particle and the second particle cannot be visually distinguished.

26. The non extractable oral solid dosage form of claim 1, wherein the first particle and the second particle are resistant to chemical separation.

* * * * *

UNITED STATES PATENT AND TRADEMARK OFFICE
CERTIFICATE OF CORRECTION

PATENT NO. : 10,624,856 B2
APPLICATION NO. : 15/884745
DATED : April 21, 2020
INVENTOR(S) : Annadurai Dharmarajan It is certified that error appears in the above-identified patent and that said Letters Patent is hereby corrected as shown below:

In the Specification

Column 4, Line 49, Table 3: Please correct "χTAMPZA ®" to read -- XTAMPZA® --

Column 18, Line 65: Please correct "0.5, 1.2," to read -- 0.5, 1, 2, --

Column 19, Line 22: Please correct "particles." to read -- particles, --

Column 19, Line 38: Please correct "3%" to read -- 1% --

Column 19, Line 46: Please correct "particles." to read -- particles, --

Column 24, Line 22: Please correct "900 ml" to read -- 900 mL --

Column 25, Line 41, Table 10: Please correct "60" to read -- 6 --

Column 25, Line 62: Please correct "maintained below" to read -- maintained below 10°C. --

In the Claims

Column 28, Lines 17-18, Claim 1: Please correct "polystilfone" to read -- polysulfone --

Column 28, Line 48, Claim 7: Please correct "is opioid" to read -- is an opioid --

Column 28, Line 54, Claim 9: Please correct "antagonist, per" to read -- antagonist per --

Column 30, Line 10, Claim 22: Please correct "0,5" to read -- 0.5 --

Column 30, Line 23, Claim 26: Please correct "non extractable" to read -- non-extractable --

Signed and Sealed this
Eighteenth Day of August, 2020

Andrei Iancu
*Director of the United States Patent and Trademark Office*